United States Patent [19]

Kons et al.

[11] Patent Number: 4,917,746
[45] Date of Patent: Apr. 17, 1990

[54] APPARATUS AND METHOD FOR CONTOURING ELASTIC RIBBON ON DISPOSABLE GARMENTS

[76] Inventors: Hugo L. Kons, 719 W. Summer, Appleton, Wis. 54911; Richard H. Frick, 1417 Winneconne, Neenah, Wis. 54956

[21] Appl. No.: 621,900

[22] Filed: Jun. 18, 1984

Related U.S. Application Data

[63] Continuation-in-part of Ser. No. 390,153, Jun. 21, 1982, abandoned.

[51] Int. Cl.⁴ .............................................. B23B 31/12
[52] U.S. Cl. .................................... 156/164; 156/204; 156/229; 156/495; 156/549; 156/554
[58] Field of Search ............ 156/163, 229, 164, 269, 156/204, 495, 494, 549, 499, 554; 226/88, 15, 3, 17, 18; 264/267; 29/121.1, 122, 129.5

[56] References Cited

U.S. PATENT DOCUMENTS

| | | | |
|---|---|---|---|
| 2,454,021 | 11/1948 | Wilson | 226/88 |
| 2,592,581 | 4/1952 | Lorig | 226/88 |
| 4,081,301 | 3/1978 | Buell | 156/164 |
| 4,227,952 | 10/1980 | Sabee | 156/204 |
| 4,293,367 | 10/1981 | Klasek et al. | 156/494 |
| 4,300,967 | 11/1981 | Sigl | 156/164 |
| 4,329,309 | 5/1982 | Kelly | 264/167 |
| 4,417,935 | 11/1983 | Spencer | 156/269 |

FOREIGN PATENT DOCUMENTS 2490079 3/1982 France .

*Primary Examiner*—Merrell C. Cashion, Jr.

[57] ABSTRACT

A method and apparatus for applying an elastic ribbon in a curved path to a continuously moving web of material. A rotatable roll is moved essentially transversely to the direction of the moving web of material. The movement of the roll is imparted to the elastic ribbon which is then adhered to the continuously moving web of material. The elastic ribbon passes around the roll with a predetermined stretch. The axis of the roll may be disposed essentially transverse to the direction of movement of the moving web or essentially perpendicular to the direction of movement of the moving web. The roll may be cylindrical in shape with a uniform radius, it may have a nonuniform radius or it may have a portion of the surface with a larger radius intermediate to the ends of the roll.

50 Claims, 2 Drawing Sheets

4,917,746

APPARATUS AND METHOD FOR CONTOURING ELASTIC RIBBON ON DISPOSABLE GARMENTS

RELATED APPLICATIONS

This application is a continuation-in-part of applicants' copending U.S. application Ser. No. 390,153, filed June 21, 1982 and now abandoned.

FIELD OF THE INVENTION

This invention relates to a method and apparatus for applying elastic ribbon to a web along a curved or undulated path and, in particular, to fabricating disposable garments such as disposable diapers having curved elastic in their leg areas.

BACKGROUND OF THE INVENTION

Use of elastic to improve the fit of reusable garments or to provide a seal at desirable locations in reusable garments is well known. Elastic in such garments is typically sewn in or confined between garment layers in either an elongated or relaxed condition. In most cases, the elastic is affixed on an individual garment by garment basis.

In disposable garments, such as disposable diapers, methods and apparatus have been developed to apply elastic ribbon at high fabricating speeds by use of an adhesive to bond the elastic ribbon to a continuous web. The web and elastic ribbon composite is subsequently cut into individual pieces for final use as elements of finished disposable garments. Because of the need for high speed and the consequent complexities of applying elastic to a web, the elastic is usually applied along a straight line. Typical arrangements for applying elastic along a straight line to a web are those shown in Buell U.S. Pat. No. 4,081,301 and Sabee U.S. Pat. No. 4,227,952. In the case of the Buell patent, the elastic and web substrate are continuously run at high speed while adhesive is intermittently applied to the elastic. The elastic and web are then brought together so that the elastic is adhered to the web at spaced apart locations. The web and elastic are then cut transversely at approximately the midpoint locations of the unadhered elastic to provide separate members for use in completing a disposable diaper. The arrangement used by Sabee entails the folding of the web substrate and the continuous application of adhesive to the elastic ribbon. The web and ribbon are then brought together and adhered to each other, except at the folded portions of the web. The elastic is then opposite the folded portions and the web is straightened. The result is a continuous web having straight elastic only in what will be the leg portions of a disposable diaper. The continuous web is then cut transversely midway between the ends of adjacent elastic strips to form separate sections for use in fabricating finished disposable diapers.

Although elastic that is straight relative to a curved portion of the body along which the disposable garment is to fit provides a better fit than if no elastic is used, considerably better results can be obtained if the elastic can be curved or contoured to follow the body curvature, for example, the curvature of the thigh and crotch area of an infant when the diaper is being worn. Although some work has been done in this area, to the inventors' knowledge, very little of the results of this work is of any practical importance. One example of a prior art approach for applying curved elastic to a disposable garment is illustrated in Bourgeois U.S. Pat. No. 3,828,367. In Bourgeois, a pair of elastic ribbons are fed to curved grooves in a roll under which a continuous web passes. As the roll with the ribbons in its grooves goes over the web the ribbons are transferred in the contoured pattern of the grooves to the roll. One problem with a grooved roll for applying elastic ribbon to a web is that a groove which is sufficiently deep to guide the ribbon is too deep to apply a flat elastic ribbon. Usually, because of the better distribution of stress in a flat tensioned ribbon, a flat ribbon is preferred in garment elasticization applications. Also, a curved groove is unreliable insofar as preventing roping and C-folding of a flat ribbon is concerned.

It is a principle object of this invention to provide a method and apparatus for undulating or curving elastic ribbon while it is continuously moving and being applied to a continuously moving web. It is a further object to accomplish the aforesaid attachment of the elastic ribbon to a web along an undulated path in a relatively simple and accurate manner.

SUMMARY OF THE INVENTION

According to the invention, an apparatus and method are provided for continuously moving thin elastic ribbon toward and into engagement with a continuously moving web. Prior to engaging the web, the elastic ribbon is provided with an oscillatory movement transverse to its length. The oscillatory movement is obtained with an oscillating means having a rotatable roll oscillating in the direction in which it is desired to oscillate the ribbon. While the roll is oscillating, the elastic ribbon is passed around a portion of the circumference of the roll to thereby impart oscillatory movement to the ribbon. The oscillating ribbon is then fed into engagement with the web and assumes an undulated or curved pattern on the web due to the oscillating movement of the ribbon. The ribbon may be maintained under tension so that the force of the tensioned ribbon together with the friction of the oscillating roll surface and the ribbon maintains the ribbon on and oscillating with the roll.

If it is desired to elasticize the leg areas of disposable garments, dual elasticating systems as described above may be utilized with the oscillations being such that the elastic ribbons are simultaneously moved toward each other and away from each other. In utilizing the continuous web and elastic composite in disposable garments, the web is cut transversely to provide separate blanks for each garment.

BRIEF DESCRIPTION OF THE DRAWINGS

Further objects and advantages of the invention will appear when taken in conjunction with the accompanying drawings, in which.

DETAILED DESCRIPTION OF THE INVENTION

Figure 1A:
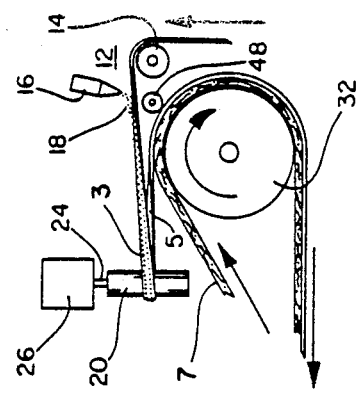
FIG. 1A is a side elevation view showing the oscillating roll in an alternate position to that shown in FIG. 1.
Figure 1B:
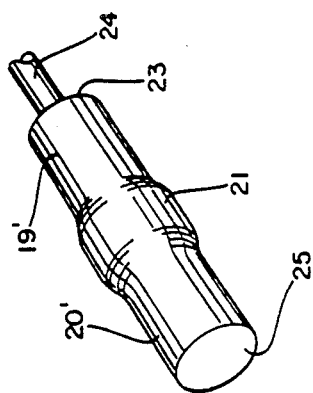
FIG. 1B is a perspective view of an oscillating roll having an alternate shape to that shown in FIGS. 1 and 1A.
Figure 1:
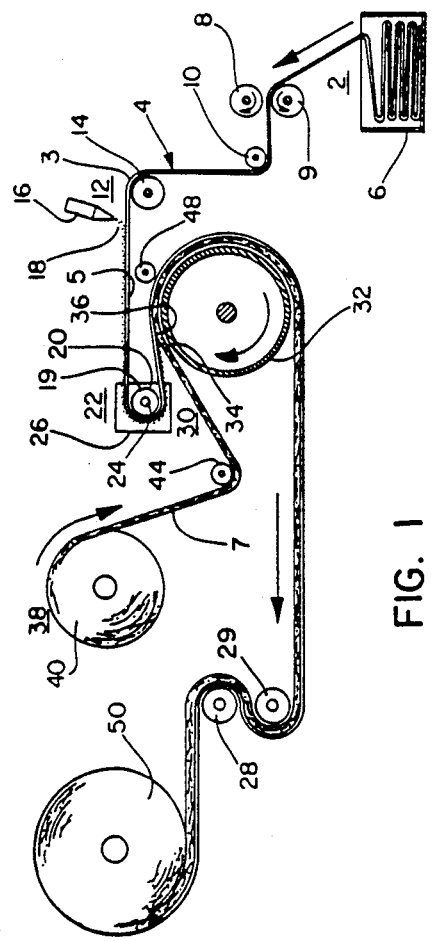
FIG. 1 is a simplified side elevation view partially in cross-section, showing the web supply, elastic application and elasticized web take-up stations of the apparatus of the invention.
Figure 2:
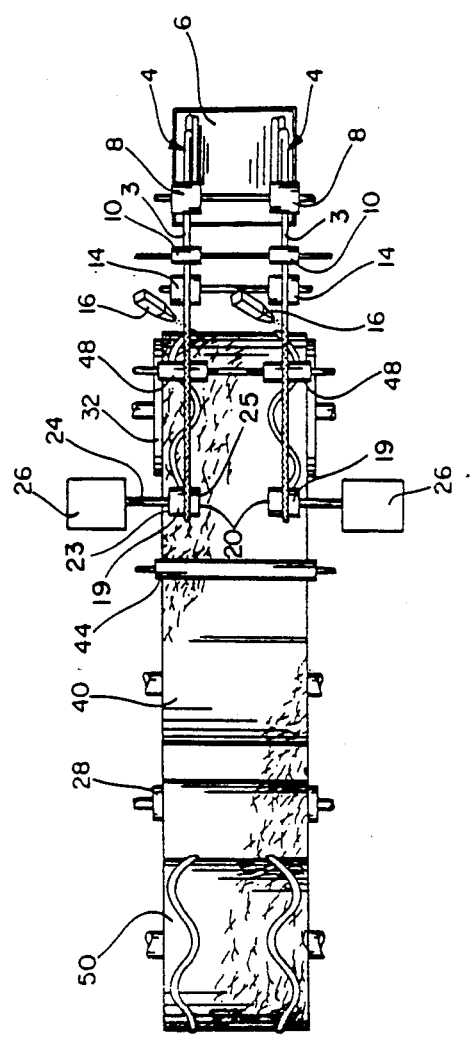
FIG. 2 is a plan view of the apparatus FIG. 1.

Referring generally to FIGS. 1 and 2, there is shown apparatus for applying a pair of elastomeric ribbons 4 to a web 7 along an undulated or curved line path. Although both of the ribbons 4 and the apparatus associated with each of them is shown in FIG. 2, only one of the ribbons and its related apparatus will be discussed herein since the ribbons and the apparatus for applying each of the ribbons to the web are substantially identical.

Relative to FIG. 1, the elastomeric ribbon 4 is relatively flat, includes wide surface 5 and 3, and has a width considerably greater than its thickness. The ribbon 4 may be supplied in a carton 6 and, if so, it will typically be natural rubber festooned within the box in such a manner that it can be pulled, tangle free, from the carton. However, the elastomeric ribbon 4 may also be of a synthetic elastomer such as "TUFTANE®", a thermoplastic polyurethane manufactured and sold by the Lord Corporation. Also, the ribbon 4, either in the form of natural rubber or a synthetic elastomer, may be supplied from a reel on which considerable amounts of the ribbon have been wound to permit continuous, high speed operation. Since, for the purposes of this invention, the use of a ribbon supply reel is not important, it has not been shown.

As shown in FIGS. 1 and 2, the apparatus for applying the elastic ribbon 4 to the web 7 includes an adhesive application station 12, an oscillating station 22, a ribbon application station 30, and a web supply station 38. Upstream of the adhesive application station 12, the nip rolls 8 and 9 pull the ribbon 4 from the carton 6 and move it around idler roll 10 toward the adhesive application station 12. At the adhesive application station 12, the ribbon 4 passes over roll 14. At, or just subsequent to the passing of the ribbon 4 over the roll 14, a line of hot melt adhesive 18 from an adhesive applicator 16 located at the station 12 is applied to the wide surface 3 of the ribbon 4. The adhesive applicator 16 is positioned a sufficient distance from an oscillating roll 20, which ribbon 4 engages at the oscillating station 22, such that the oscillating roll 20 does not impart lateral oscillating movement to the ribbon 4 at the point of application of adhesive 18 by applicator 16 to the ribbon 4. The roll 14, insofar as its function relating to the application of the adhesive 18 to the ribbon 4 is concerned, acts to maintain the ribbon 4 on a straight line path while the adhesive is being applied to the ribbon 4 by the applicator 16.

The ribbon 4, with at least one line of adhesive 18 on its wide surface 3, continues on to the oscillating station 22 where it engages the circumferential surface 19 of the oscillating roll 20 between the ends 23 and 25 of the roll and passes around the roll 20. The oscillating movement of the roll 20 causes the ribbon 4 to oscillate in a direction transverse to the length of the roll as the ribbon passes around the roll 20 and continues on to the chill roll 32 at the ribbon application station 30. The oscillating roll 20 has an axial shaft 24 about which it freely rotates as the ribbon 4 passes in engagement with the roll. An oscillating or reciprocating mechanism 26 is connected to the shaft 24 of the oscillating roll 20 for moving the roll 20 in an oscillating or reciprocating manner. In the embodiment of FIGS. 1 and 2, the oscillating motion is in a direction substantially parallel to the axial shaft 24. The oscillating mechanism may be of a type well-known in the art and consequently will not be further described herein.

The oscillating roll may be disposed such that its axial shaft is not in a horizontal plane and, in FIG. 1A, the oscillating roll 20 is shown disposed in a substantially vertical position relative to the side elevation view of FIG. 1A. The axial shaft 24 of the roll 20 is connected to an oscillating mechanism 26 which functions to provide oscillatory movement to the roll 20 in a direction substantially perpendicular to the axial shaft 24 of the roll 20. This movement is also perpendicular to the wide surfaces 3 and 5 of the ribbon 4 during a portion of their travel around the roll 20. As may be seen in FIG. 1A, the ribbon 4 rotates 90° as it approaches the roll 20 from the roll 14, passes around the roll 20 with the wide surface 5 of the ribbon 4 in contact with the roll 20 and continues on toward the rotatably driven chill roll 32. As in the embodiment of FIGS. 1 and 2, the oscillating roll 20 imparts oscillatory movement to the ribbon 4 in a direction transverse to the length of the ribbon 4.

Another embodiment of the oscillating roll is shown in FIG. 1B in which the elements which differ from those shown in FIG. 1 are identified with a prime designation. The oscillating roll 20' shown in FIG. 1B has a circumferential surface 19' including a raised area or crown 21 around the entire surface 19'. The crown 21 is positioned intermediate the end 23 and 25 of the roll 20'. The ribbon 4 engages and stays on the crown 21 as it passes around and oscillates with the roll 20". The reason that the ribbon 4 stays on the crown 21 is that the lateral forces on the ribbon 4 balance in opposite directions at the high point of the crown 21. Thus, the ribbon 4 will resist the lateral force due to the oscillation movement which tends to move the ribbon axially on the roll, and ride on the crown 21 and thereby oscillate with the roll 20'.

Referring again to FIGS. 1 and 2, at the web supply station 38, a continuous length of web 7 is supplied from web supply roll 40. The web 7 passes around an idler roll 44, which positions the web 7 for engagement at the desired location with chill roll 32 as the web 7 moves toward ribbon application station 30. At station 30, the web 7 engages the chill roll 32 at point 34 and thereby becomes somewhat chilled prior to engaging the ribbon 4 at point 36. After their engagement at point 36, the web 7 and ribbon 4 continue onward together along the surface of chill roll 32 and between the nip formed by chill roll 32 and nip roll 48.

As may be appreciated, the oscillatory motion imparted to the ribbon 4 transversely to its length by the oscillating roll 20 causes the ribbon 4 to engage the web 7 along an undulated path. The ribbon 4 is firmly bonded to the web 7 while in the undulated path due to the force applied to the ribbon 4 and web 7 between the nip of chill roll 32 and nip roll 48. The engagement of the web 7 with the chill roll 32 between points 34 and 36 along the surface of the chill roll 32 cools the web 7 to minimize the likelihood of the burning of the web when it is engaged by the line 18 of hot melt adhesive on the ribbon 4. Similarly, the engagement of the ribbon 4 and the web 7 along the surface of the chill roll 32 permits the cooling of the adhesive 18 to thereby avoid burning of the web 7 the ribbon 4 and web 7 are firmly compressed together by the nip roll 48.

Considering again the tensioning and stretching of the elastic ribbon 4, the velocity of the chill roll 32 and nip roll 48 exceeds the velocity of the nip rolls 8 and 9 to thereby stretch the ribbon 4. The extent of the stretch may vary but, for purposes of elasticizing leg areas of disposable diapers, the stretch should be about 100%. Moreover, the stretch of the ribbon 4 as it passes over the surface 19 of the roll 20 and the friction between the surface 19 and the ribbon 4 should be sufficient to ensure that the ribbon 4 will closely follow the oscillating movement of the roll 20 and thereby provide the desired undulated pattern of the ribbon 4 on the web 7. A 100% stretch of the ribbon 4 is satisfactory in this regard.

After the web 7 and the ribbon 4 leave the chill roll 32, the composite structure may pass on to the next step in the fabricating of the disposable garment or, as shown in FIGS. 1 and 2, the composite web 7 and ribbon 4 may be drawn through drive rolls 28 and 29 and wound on to a take-up roll 50 for use at a later time in the fabrication of a garment. It may be noted that the rolls 28 and 29 are driven at a speed sufficient to maintain the desired stretch in the ribbon 4 as determined by the speed of the rolls 32 and 48 relative to the speed of the rolls 8 and 9.

Figure 4:
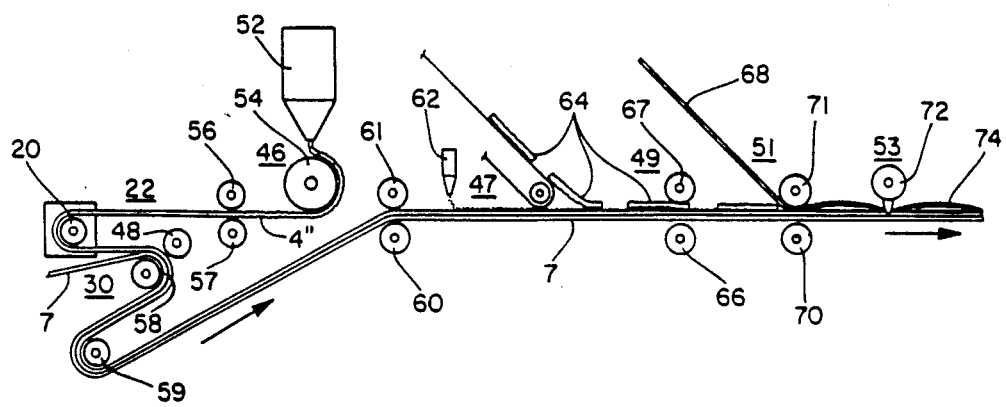
FIG. 4 is a side elevation view of an alternate embodiment of the invention illustrating apparatus for fabricating disposable diapers in accord with the invention.

Referring now to FIG. 4, an embodiment of the invention is shown in which the elastic ribbon is supplied by an extruder and the web and undulated ribbon composite is fed directly to a disposable diaper manufacturing apparatus. In FIG. 4, those elements which differ from the elements shown in FIGS. 1 and 2 are identified with a "double prime" designation. The apparatus illustrated in FIG. 4 includes an elastic ribbon supply station 46, an oscillator station 22, a ribbon application station 30, a diaper adhesive application station 47, an absorbent pad application station 49, a liner web application station 51, and a cutting station 53. The extruder 52 is located at the ribbon supply station 46 and extrudes a substantially flat continuous length of elastic ribbon 4" on to a rotating chill roll 54. The ribbon 4" is continuously drawn from the chill roll 54 and fed to the oscillator roll 20 by drive rolls 56 and 57. The drive rolls 56 and 57 are driven by suitable means (not shown) at a speed sufficiently faster than the rotational speed of the chill roll 54 to maintain the ribbon 4" under tension. The elastic ribbon 4" is preferably of a pressure sensitive adhesive elastomeric such as "Fullastic ®" elastomer, manufactured by the H. B. Fuller Company. After the ribbon 4" is extruded by the extruder 52, it passes around a portion of the circumference of the chill roll 54 thereby causing the ribbon 4" to solidify. Tension may then be maintained on the ribbon 4" as it is oscillated by the oscillating roll 20 and fed to the applicator roll 58 at ribbon application station 30. As previously mentioned, the ribbon 4" has pressure sensitive adhesive properties. Consequently, the ribbon 4" is bonded to the web 7 at the ribbon applicator station 30 by application of pressure to the ribbon 4" and web 7 by rolls 58 and nip roll 48. Thus, bonding of the ribbon 4" and web 7 together does not require an adhesive and therefore the problems of applying the adhesive to a transversely oscillating ribbon are eliminated.

Figure 3:
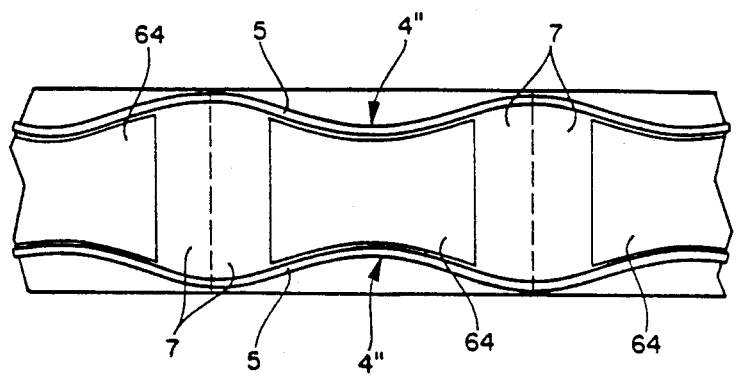
FIG. 3 is a plan view of the elasticized web fabricated with the use of the apparatus and method of the invention.

Subsequent to the bonding of the ribbon 4" and web 7 together at the ribbon application station 30, the web and ribbon composite pass around an idler roll 59 and are driven toward the diaper adhesive application station 47 by a pair of drive rolls 60 and 61 which operate at a speed relative to the applicator roll 58 to maintain the web 7 and ribbon 4" under tension and the ribbon 4" extended. At the adhesive application station 47, an adhesive applicator 62 applies adhesive to the web 7 for purposes of bonding additional components to the web 7. At the absorbent pad application station 49, discrete absorbent pads 64 are applied to the 7 at locations adjacent the portions of the ribbon 4" (see FIG. 3) that are toward the longitudinal centerline of the web 7 and nipped to the web by the nip rolls 66 and 66'. Following the placing of the absorbent pads 64 on to the web 7, a continuous web 68 of diaper liner material is applied over the pads 64 to the web 42 and nipped tightly to the web 7 by nip rolls 70 and 70'. As a result, a continuous web sandwich is formed which comprises the web 7, the discrete absorbent pads 64 spaced apart along the length of the web 7, and the liner 68. For purposes of fabricating disposable diapers, the web 7 is preferably a fluid impervious plastic film and the liner web 68 is a fluid permeable material. Following the application of the liner web 68 to the web 7 at the station 51, the composite web continues to a cutting station 53. At the cutting station 53 a web cutter 72 cuts the webs 7 and 68 between the spaced apart absorbent pads 64 to form individual disposable diapers 74.

An apparatus and method for applying elastic ribbon having a curved or undulated path to a continuously moving web has been described. The web and elastic composite may be stored for later use, for example, by winding the web and ribbon on to a reel. Alternatively, the web and ribbon may be used immediately in the fabrication of disposable garments such as disposable diapers. When used in a disposable diaper, the curved elastic in each individual diaper fabricated from the web and elastic ribbon composite provides elastic strips which are contoured to fit the shape of the body on which the diaper is worn and thereby provide a better fit or seal of the diaper against the body. Moreover, the benefit of the method and apparatus of this invention may be obtained while manufacturing elasticized disposable diapers or other disposable garments at very high production speeds.

It will be understood that the foregoing description of the present invention is for purposes of illustration only and that the invention is susceptible to a number of modifications or changes none of which entail any departure from the spirit and scope of the present invention as defined in the hereto appended claims.

What is claimed is:

1. A method for applying a continuous, moving ribbon of elastic material to a moving web of material, comprising the steps of:
    rotatably mounting at least one receiving roll about an axis essentially perpendicular to the surface of the web;
    continuously moving the web in a direction coinciding with its length;
    simultaneously moving and applying tension to the elastic ribbon in the direction of its length around a circumferential surface of the receiving roll;
    oscillating said receiving roll in a direction essentially transverse to the direction of movement of the web while the ribbon is contacting said circumferential surface, imparting a coefficient of friction such that the friction of said surface with the ribbon and the tension of the ribbon together provide sufficient force on the ribbon to move the ribbon around said surface and slidingly along said rotational axis of said receiving roll in an oscillatory manner with the oscillatory motion of said receiving roll, said receiving roll being of a sufficient length to contain the axial travel of the ribbon thereacross; feeding the oscillating ribbon into engagement with the web in an undulating pattern and adhering the ribbon thereto.

2. An apparatus for applying a continuous moving ribbon of elastic material to a moving web of material, comprising:

means for continuously moving the web in a direction coinciding with its length;

at least one receiving roll for receiving the elastic ribbon, said roll being rotatably mounted about an axis essentially perpendicular to the surface of the web;

oscillatory means for imparting oscillatory movement to said roll in a direction essentially transverse to the direction of movement of the web;

means for moving the elastic ribbon in the direction of its length;

and means for applying tension to the ribbon while the ribbon is moving around said oscillatory roll;

said oscillatory roll having a circumferential surface engaging the ribbon, said surface having a coefficient of friction such that the friction of said surface with the ribbon and the tension in the ribbon together provide sufficient force on the ribbon to move the ribbon around said circumference and along said rotational axis of said receiving roll in an oscillatory manner with the oscillatory motion of said receiving roll, said roll being of a sufficient length to contain the oscillatory travel of the ribbon longitudinally across the circumference thereof; and engagement means for bringing the oscillating ribbon and the web into engagement with one another.

3. An apparatus, as recited in claim 2, wherein said axis of said roll is essentially transverse to said direction of movement of said web.

4. An apparatus, as recited in claim 3, wherein said roll has a circumferential surface area in contact with said elastic ribbon, said surface area having a coefficient of friction whereby said coefficient of friction, said surface area and said predetermined tension provide a sufficient force to transfer said transverse movement from said roll to said elastic ribbon.

5. An apparatus, as recited in claim 2, wherein said axis of said roll is essentially perpendicular to said direction of movement of said web.

6. An apparatus, as recited in claim 4 or 5, wherein said means for applying a predetermined tension comprises means for providing a predetermined stretch to said elastic ribbon.

7. An apparatus, as recited in claim 6, wherein said means for providing a predetermined stretch to said elastic ribbon comprises:

a first pair of rolls rotating at a first speed, upstream from said roll, through which said elastic ribbon constrictively passes;

a second pair of rolls rotating at a second speed, disposed downstream from said roll, through which said elastic ribbon constrictively passes; and wherein said second speed is greater than said first speed.

8. An apparatus, as recited in claim 1 or 7, wherein said means for attaching said elastic ribbon to said continuously moving web comprises:

means for contacting said elastic ribbon, after passing around said roll, with said continuously moving web; and means for adhering said elastic ribbon to said continuously moving web.

9. An apparatus, as recited in claim 8, wherein said means for contacting said elastic ribbon with said continuously moving web comprises said second pair of rolls wherein said elastic ribbon and said continuously moving web are simultaneously passed through said second pair of rolls.

10. An apparatus, as recited in claim 9, wherein said means for adhering said elastic ribbon to said continuously moving web comprises said elastic ribbon having pressure sensitive adhesive properties.

11. An apparatus, as recited in claim 10, wherein said elastic ribbon comprises an extruded elastic ribbon and wherein said apparatus further comprises means for extruding said extruded elastic ribbon.

12. An apparatus, as recited in claim 11, further comprising means for exerting pressure to said elastic ribbon and said continuously moving web.

13. An apparatus, as recited in claim 12, wherein said means for exerting pressure to said elastic ribbon and said continuously moving web comprise said second pair of rolls wherein said second pair of rolls are spaced at a distance apart whereby the simultaneous constrictively passing through of said elastic ribbon and said continuously moving web activates said pressure sensitive adhesive properties of said elastic ribbon.

14. An apparatus, as recited in claim 9, wherein said means for adhering said elastic ribbon to said continuously moving web comprises means for applying an adhesive to said elastic ribbon.

15. An apparatus, as recited in claim 14, wherein said adhesive is a hot melt adhesive and said means for adhering further comprises chilling means for chilling said continuously moving web.

16. An apparatus, as recited in claim 15, wherein said means for applying said hot melt adhesive is upstream of said roll and downstream of said first pair of rolls.

17. An apparatus, as recited in claim 16, wherein said chilling means comprises one of said second pair of rolls.

18. An apparatus, as recited in claim 16, further comprising means for causing said continuously moving web to contact said chilling means prior to contacting said elastic ribbon.

19. An apparatus, as recited in claim 1 or 18, wherein said roll comprises a roll having a cylindrical surface, first and second ends and a uniform radius between said first and second ends.

20. An apparatus, as recited in claim 1 or 18, wherein said roll comprises a roll having a cylindrical surface, first and second ends and a nonuniform radius between said first and second ends.

21. An apparatus, as recited in claim 20, wherein said nonuniform radius comprises a first radius adjacent to said first and second ends and a second radius intermediate said first and second ends.

22. An apparatus, as recited in claim 21, wherein said second radius is greater than said first radius.

23. An apparatus, as recited in claim 1 or 22, wherein said means for imparting movement to said roll comprises means for imparting a curved line path to said elastic ribbon relative to said continuously moving web.

24. An apparatus, as recited in claim 1 or 22, wherein said means for imparting movement to said roll comprises means for imparting an undulating path to said elastic ribbon relative to said continuously moving web.

25. An apparatus, as recited in claim 1 or 22, wherein said means for imparting movement to said roll comprises means for imparting an oscillating path to said elastic ribbon relative to said continuously moving web.

26. A method for applying an elastic ribbon in a curved line path to a surface of a web of material, comprising the steps of:
- continuously moving the web of material in a direction coinciding with its length;
- imparting movement to a single roll which is rotatable about its axis, wherein the movement is essentially transverse to the direction of movement of the web of material and wherein the transverse movement is parallel to the surface of the web;
- passing an elastic ribbon around the single roll whereby the transverse movement of the roll is imparted to the elastic ribbon; and
- attaching the elastic ribbon to the surface of the web of material.

27. A method, as recited in claim 26, wherein the axis of the roll is disposed essentially transverse to the direction of movement of the continuously moving web.

28. A method, as recited in claim 26, wherein the axis of the roll is disposed essentially perpendicular to the direction of movement of the continuously moving web.

29. A method, as recited in claim 27 or 28, wherein the step of passing an elastic ribbon around the roll further comprises the step of applying a predetermined tension to the elastic ribbon while the elastic ribbon is passing around the roll.

30. A method, as recited in claim 29 wherein the step of applying a predetermined tension to the elastic ribbon comprises applying a predetermined stretch to the elastic ribbon.

31. A method, as recited in claim 30, wherein the step of applying a predetermined stretch to said elastic ribbon comprises the steps of:
- constrictively passing the elastic ribbon through a first pair of rolls rotating at a first speed, upstream from the roll;
- constrictively passing the elastic ribbon through a second pair of rolls rotating at a second speed, downstream from the roll; and
- wherein the second speed is greater than the first speed.

32. A method, as recited in claim 31, further comprising the steps of rotating the second pair of rolls at a speed relative to the first set of rolls whereby the stretch of the elastic ribbon is essentially 100%.

33. A method as recited in claim 26 or 32, wherein the step of attaching the elastic ribbon to the continuously moving web, comprises the steps of:
- contacting the elastic ribbon, after passing around the roll, with the continuously moving web; and
- adhering the elastic ribbon to the continuously moving web.

34. A method, as recited in claim 33, wherein the step of contacting the elastic ribbon with the continuously moving web is accomplished by simultaneously constrictively passing the elastic ribbon and the continuously moving web through the second pair of rolls.

35. A method, as recited in claim 34, wherein the step of adhering the elastic ribbon to the continuously moving web is accomplished by providing an elastic ribbon with pressure sensitive adhesive properties.

36. A method, as recited in claim 35, wherein the step of providing an elastic ribbon with pressure sensitive adhesive properties is accomplished by providing an extruded elastic ribbon with pressure sensitive adhesive properties.

37. A method, as recited in claim 36, further comprising the step of exerting pressure on the elastic ribbon and continuously moving web sufficient to activate the pressure sensitive adhesive properties of the elastic ribbon.

38. A method, as recited in claim 36, wherein the step of exerting pressure is accomplished by simultaneously constrictively passing the elastic ribbon and continuously moving web through the second pair of rolls.

39. A method, as recited in claim 34, wherein the step of adhering the elastic ribbon to the continuously moving web comprises the step of applying an adhesive to the elastic ribbon.

40. A method, as recited in claim 39, wherein the step of applying an adhesive comprises the step of applying a hot melt adhesive to the elastic ribbon.

41. A method, as recited in claim 40, further comprising the step of chilling the continuously moving web.

42. A method, as recited in claim 40, wherein the step of applying the adhesive to the elastic ribbon is accomplished by applying the adhesive upstream of the roll and downstream of the first pair of rolls.

43. A method, as recited in claim 42, wherein the step of chilling the continuously moving web is accomplished by chilling the continuously moving web before the step of contacting with the elastic ribbon is accomplished.

44. A method, as recited in claim 43, wherein the roll comprises a cylindrically shaped roll with first and second ends and a uniform radius between the first and second ends.

45. A method, as recited in claim 43, wherein the roll comprises a cylindrically shaped roll with first and second ends and a nonuniform radius between the first and second ends.

46. A method, as recited in claim 43, wherein the roll comprises a cylindrically shaped roll with first and second ends and a first radius adjacent to the first and second ends and a second radius intermediate the first and second ends.

47. A method, as recited in claim 46, wherein the second radius is greater than the first radius.

48. A method, as recited in claim 26, 44, 45 or 47 wherein the step of imparting movement to a roll is accomplished by imparting a curved line path to the elastic ribbon relative to the continuously moving web.

49. A method, as recited in claim 26, 44, 45 or 47, wherein the step of imparting movement to a roll is accomplished by imparting an undulating path to the elastic ribbon relative to the continuously moving web.

50. A method, as recited in claim 26, 44, 45 or 47, wherein the step of imparting movement to a roll is accomplished by imparting an oscillating path to the elastic ribbon relative to the continuously moving web.

* * * * *